United States Patent [19]

Ikesu et al.

[11] Patent Number: 5,187,057
[45] Date of Patent: Feb. 16, 1993

[54] SILVER HALIDE COLOR PHOTOGRAPHIC LIGHT-SENSITIVE MATERIAL AND COLOR PHOTOGRAPHIC COUPLER

[75] Inventors: Satoru Ikesu, Hino; Hiroshi Kita, Hachioji; Yutaka Kaneko, Sagamihara, all of Japan

[73] Assignee: Konica Corporation, Tokyo, Japan

[21] Appl. No.: 840,278

[22] Filed: Feb. 24, 1992

[30] Foreign Application Priority Data

Feb. 26, 1991 [JP] Japan .................................. 3-53226

[51] Int. Cl.$^5$ ............................................ G03C 7/38
[52] U.S. Cl. ................................. 430/558; 430/384; 430/385
[58] Field of Search .................... 430/558, 384, 385

[56] References Cited

U.S. PATENT DOCUMENTS 4,970,142 11/1990 Kaneko ............................ 430/558

FOREIGN PATENT DOCUMENTS 2190850 7/1990 Japan .................................. 430/558

*Primary Examiner*—Lee C. Wright
*Attorney, Agent, or Firm*—Finnegan, Henderson, Farabow, Garrett and Dunner

[57] ABSTRACT

A silver halide color photographic material is disclosed. The material contains a coupler represented by a formula

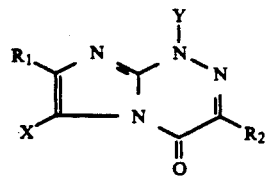

wherein $R_1$, $R_2$ and Y independently represent a hydrogen atom or substituent, X represents a hydrogen atom or an atom or group capable of splitting off upon reaction with the oxidation product of a color developing agent. The dye images formed with the coupler of the present invention are fast to heat, moisture and light.

8 Claims, No Drawings

SILVER HALIDE COLOR PHOTOGRAPHIC LIGHT-SENSITIVE MATERIAL AND COLOR PHOTOGRAPHIC COUPLER

BACKGROUND OF THE INVENTION

The present invention relates to a silver halide color photographic light-sensitive material and a new photographic coupler used as a material therefor. More specifically, the present invention relates to a photographic cyan coupler which forms dye images having excellent fastness to heat/moisture and light.

SUMMARY OF THE INVENTION

It is an object of the present invention to provide a new photographic cyan coupler used as a material for color photographic light-sensitive materials.

It is another object of the present invention to provide a photographic coupler which forms cyan dye images showing no hue change due to exposure to heat/moisture or light.

It is still another object of the present invention to provide a silver halide photographic light-sensitive material which gives dye images stable to heat/moisture and light.

The photographic coupler for the present invention is represented by the formula I:

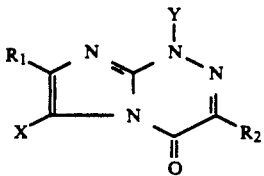

wherein
$R_1$, $R_2$ and Y independently represent a hydrogen atom or substituent.

X represents a hydrogen atom or an atom or group capable of splitting off upon reaction with the oxidation product of a color developing agent.

$R_1$ and $R_2$ independently represent a hydrogen atom or substituent. Typical examples of the substituent represented by $R_1$ or $R_2$ include alkyl, aryl, anilino, acylamino, sulfonamide, alkylthio, arylthio, alkenyl and cycloalkyl groups. Also included are halogen atoms, cycloalkenyl, alkinyl, heterocyclic, sulfonyl, sulfinyl, phosphonyl, acyl, carbamoyl, sulfamoyl, cyano, alkoxy, sulfonyloxy, aryloxy, heterocyclic oxy, siloxy, acyloxy, carbamoyloxy, amino, alkylamino, imide, ureide, sulfamoylamino, alkoxycarbonylamino, aryloxycarbonylamino, akloxycarbonyl, aryloxycarbonyl, heterocyclic thio, thioureide, carboxyl, hydroxy, mercapto, nitro and sulfonic acid groups, and spiro compound groups and bridged hydrocarbon compound groups.

The alkyl group represented by $R_1$ or $R_2$ preferably has 1 to 32 carbon atoms, whether linear or branched.

The aryl group represented by $R_1$ or $R_2$ is preferably a phenyl group.

Examples of the acylamino group represented by $R_1$ or $R_2$ include alkylcarbonylamino groups and arylcarbonylamino groups.

Examples of the sulfonamide group represented by $R_1$ or $R_2$ include alkylsulfonylamino groups and arylsulfonylamino groups.

The alkyl moiety and aryl moiety in the alkyl thio group and arylthio group represented by $R_1$ or $R_2$ include the above-mentioned alkyl groups and aryl groups.

The alkenyl group represented by $R_1$ or $R_2$ preferably has 2 to 32 carbon atoms. The cycloalkyl group represented by $R_1$ or $R_2$ preferably has 3 to 12, particularly 5 to 7 carbon atoms. The alkenyl group may be linear or branched.

The cycloalkenyl group represented by $R_1$ or $R_2$ preferably has 3 to 12, particularly 5 to 7 carbon atoms.

Examples of the sulfonyl group represented by $R_1$ or $R_2$ include alkylsulfonyl groups and arylsulfonyl groups.

Examples of the sulfinyl group represented by $R_1$ or $R_2$ include alkylsulfinyl groups and arylsulfinyl groups.

Examples of the phosphonyl group represented by $R_1$ or $R_2$ include alkylphosphonyl groups, alkoxyphosphonyl groups, aryloxyphosphonyl groups and arylphosphonyl groups.

Examples of the acyl group represented by $R_1$ or $R_2$ include alkylcarbonyl groups and arylcarbonyl groups.

Examples of the carbamoyl group represented by $R_1$ or $R_2$ include alkylcarbamoyl groups and arylcarbamoyl groups.

Examples of the sulfamoyl group represented by $R_1$ or $R_2$ include alkylsulfamoyl groups and arylsulfamoyl groups.

Examples of the acyloxy group represented by $R_1$ or $R_2$ include alkylcarbonyloxy groups and arylcarbonyloxy groups.

Examples of the carbamoyloxy group represented by $R_1$ or $R_2$ include alkylcarbamoyloxy groups and arylcarbamoyloxy groups.

Examples of the ureide group represented by $R_1$ or $R_2$ include alkylureide groups and arylureide groups.

Examples of the sulfamoylamino group represented by $R_1$ or $R_2$ include alkylsulfamoylamino groups and arylsulfamoylamino groups.

The heterocyclic group represented by $R_1$ or $R_2$ is preferably a 5- to 7-membered ring, including a 2-furyl group, 2-thienyl group, 2-pyrimidinyl group, 2-benzothiazolyl group, 1-pyrrolyl group and 1-tetrazolyl group.

The heterocyclic oxy group represented by $R_1$ or $R_2$ preferably has a 5- to 7-membered heterocyclic ring, including a 3,4,5,6-tetrahydropyranyl-2-oxy group and 1-phenyltetrazol-5-oxy group.

The heterocyclic thio group represented by $R_1$ or $R_2$ is preferably a 5- to 7-membered heterocyclic thio group, including a 2-pyridylthio group, 2-benzothiazolylthio group and 2,4-diphenoxy-1,3,5-triazole-6-thio group.

Examples of the siloxy group represented by $R_1$ or $R_2$ include a trimethylsiloxy group, triethylsiloxy group and dimethylbutylsiloxy group.

Examples of the imide group represented by $R_1$ or $R_2$ include an succinimide group, 3-heptadecylsuccinimide group, phthalimide group and glutarimide group.

Examples of the spiro compound group represented by $R_1$ or $R_2$ include spiro[3.3]heptan-1-yl.

Examples of the bridged hydrocarbon compound group represented by $R_1$ or $R_2$ include bicyclo[2.2.1]heptan-1-yl, tricyclo[3.3.1.1$^{3,7}$]decan-1-yl and 7,7-dimethylbicyclo[2.2.1]heptan-1-yl.

These groups may have an additional non-diffusible substituent such as a long-chain hydrocarbon group or polymer group.

Examples of the group capable of splitting off upon reaction with the oxidation product of a color developing agent, represented by X, include halogen atoms such as atoms of chlorine, bromine and fluorine, and alkoxy, aryloxy, heterocyclic oxy, acyloxy, sulfonyloxy, alkoxycarbonyloxy, aryloxycarbonyl, alkyloxyaryloxy, alkoxyoxyaryloxy, alkylthio, arylthio, heterocyclic thio, alkyloxythiocarbonylthio, acylamino, sulfonamide, nitrogen-containing heterocyclic rings bound via nitrogen atom, alkyloxycarbonylamino, aryloxycarbonylamino, carboxyl,

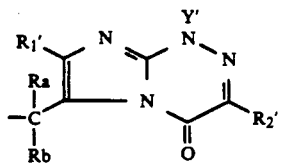

wherein $R_1'$, $R_2'$ and $Y'$ have the same definitions as $R_1$, $R_2$ and $Y$ in Formula I; Ra and Rb independently represent a hydrogen atom, aryl group, alkyl group or heterocyclic group. X is preferably a hydrogen atom or chlorine atom.

With respect to Formula I, Y represents a hydrogen atom or substituent, which is the group which splits off from the compound of the present invention upon its reaction with the oxidation product of a developing agent. Examples of the substituent represented by Y include the group described in Japanese Patent Publication Open to Public Inspection (hereinafter referred to as Japanese Patent O. P. I. Publication) No. 228444/1986, which is capable of splitting off under alkaline conditions, and the substituent described in Japanese Patent O. P. I. Publication No. 133734/1981, which couples off upon reaction with the oxidation product of a developing agent. Y is preferably a hydrogen atom.

The compound represented by Formula I is more preferably represented by the formula II:

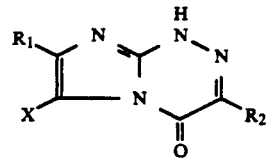

wherein $R_1$, $R_2$ and Y have the same definitions as $R_1$, $R_2$ and Y for the compound represented by Formula I.

Typical examples of the compound of the present invention are given below.

| No. | R₁ | R₂ | X |
|---|---|---|---|
| 1 | —CH₃ | H | Cl |
| 2 | —C₆H₅ | H | H |
| 3 | —NHC₁₂H₂₅ | —CH₃ | H |
| 4 | 4-(C₁₂H₂₅O)-C₆H₄-NHSO₂-C₆H₄- | H | Cl |
| 5 | CH₃-CH(CH₂)₂NHCO(CH₂)₃O-C₆H₄-(C₁₅H₃₁) | —OCH₃ | Cl |
| 6 | 4-CH₃-C₆H₄-NHCOCHO(C₆H₁₃)-C₆H₃(C₅H₁₁(t))(C₅H₁₁(t))-SCH₂- | H | Cl |
| 7 | C₁₁H₂₃SO₂NH-C₆H₄-SO₂- | —NHCOCH₃ | H |
| 8 | 4-(C₁₈H₃₇O)-C₆H₄-NH- | —NHCO-C₆H₅ | Br |
| 9 | —OC₁₂H₂₅ | H | Cl |

-continued

| No. | R₁ | R₂ | X |
|---|---|---|---|
| 10 | -NHCONH-C₆H₄-C₁₁H₂₃ | -C₂H₅ | H |
| 11 | -CONHC₁₂H₂₅ | -C₆H₁₁ (cyclohexyl) | Cl |
| 12 | -SO₂N(C₈H₁₇)₂ | -CH₃ | H |
| 13 | -C₆H₄-NHCOC₁₃H₂₇ (para) | -C₆H₁₁ (cyclohexyl) | Cl |
| 14 | -COCH₂-C₆H₄-CH₃ | -C₆H₅ | H |
| 15 | -CH₃ | H | H |
| 16 | -CH(CH₃)₂ | -C₆H₄-NHSO₂C₁₂H₂₅ | Cl |
| 17 | (3-C₄H₉(t)-4,5-methylenedioxyphenyl)-NHCOCH(C₁₂H₂₅)-C₆H₄-CH₃ | H | Cl |

-continued

| No. | R₁ | R₂ | X |
|---|---|---|---|
| 18 | 2-(OC₁₂H₂₅)C₆H₄— | —NHCOC₆H₅ | Br |
| 19 | —C₁₂H₂₅ | furan (5-methyl-2-furyl) | H |
| 20 | C₆H₅— | —NO₂ | H |
| 21 | —SCH₃ (H) | Cl | Cl |
| 22 | —SCH₃ | Cl | H |
| 23 | 4-(OC₁₂H₂₅)-2-(NHSO₂)C₆H₃— | —CH₃ | H |
| 24 | 4-Cl-2-(NHSO₂)C₆H₃— | —CH₃ | H |
| 25 | —C(CH₃)₂CH₂SO₂C₁₈H₃₇ | H | Cl |
| 26 | —C₁₅H₃₁ | —NHCOC₁₃H₂₇ | —OCH₃ |
| 27 | —NHC₆H₅ | Br | H |

-continued
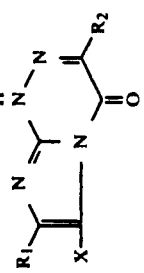
| No. | R₁ | R₂ | X |
|---|---|---|---|
| 28 | 3-NHCOC₁₁H₂₃-phenyl | Cl | H |
| 29 | phenyl | 4-(-S-)phenyl | H |
| 30 | phenyl | 4-(-SO₂-)phenyl | H |
| 31 | H | H | Cl |
| 32 | —CH₃ | 3-NHCOC₁₁H₂₃-phenyl | Cl |
| 33 | 4-[CH₃CH(CH₂)₂O]-C₆H₄-C₁₅H₃₁ | 2-(1,4-dioxanyl) | H |
| 34 | —C(CH₃)₃ | 2-CH₃, NHSO₂C₈H₁₇-phenyl | Cl |

-continued
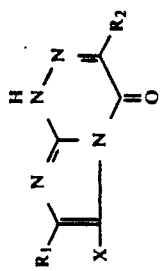
| No. | R₁ | R₂ | X |
|---|---|---|---|
| 35 | —C₁₆H₃₃ | —C₄H₉(t) | phenoxy |
| 36 | —SO₂CH₂C₆H₅ | 2-OC₁₂H₂₅-phenyl | —OCH₃ |
| 37 | —NHCOCH₃ | 2-(NHCOCHO-C₄H₉)-4-C₅H₁₁(t)-phenyl | Cl |
| 38 | phenyl-NH— | 3-methylphenyl-NHCOCH₂O-[2-C₅H₁₁(t)-4-C₅H₁₁(t)-phenyl] | 4-OCH₃-phenyl-S— |
| 39 | —OC₂H₅ | 2-methyl-(NHSO₂C₁₂H₂₅)-phenyl | Cl |

-continued
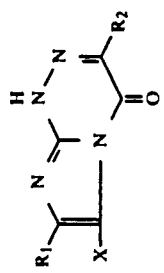
| No. | R₁ | R₂ | X |
|---|---|---|---|
| 40 | —C₆H₅ | (2-CH₃-phenyl)-NHSO₂C₁₂H₂₅ | 3-chloro-4-methoxy-phenoxy with NO₂ at 4' (2-Cl, 4-NO₂-phenoxy) |
| 41 | —SO₂N(C₃H₇)₂ | 3-C₈H₁₇-5-OC₄H₉-phenyl with —NHSO₂— linkage | —OCH₂—C₆H₅ |
| 42 | —SO₂NHC₁₂H₂₅ | cyclohexyl (H) | Cl |
| 43 | —COOCH₃ | —NHCOC₁₅H₃₁ | pyrazol-1-yl |
| 44 | —COCH₃ | —NHC₁₈H₃₇ | H |
| 45 | 3-(NHCOC₁₈H₃₇)-benzyl (—CH₂—C₆H₄—NHCOC₁₈H₃₇) | —C₆H₅ | Cl |

-continued
| No. | $R_1$ | $R_2$ | X |
|---|---|---|---|
| 46 | —CH₃ | 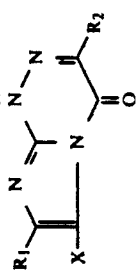 | |
| 47 | | | 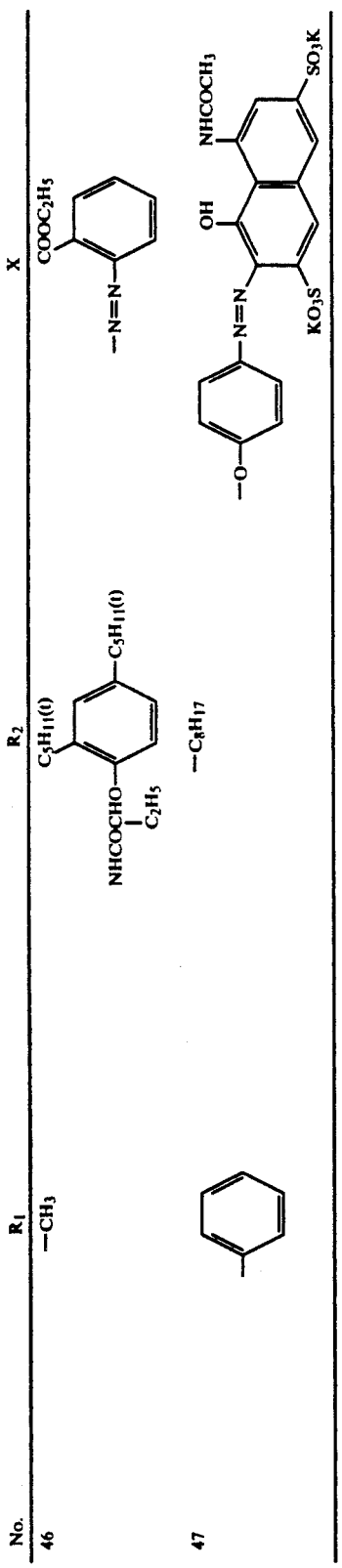 |

The coupler of the present invention includes the compound described in the Journal of Organic Chemistry, 1988, Vol. 53 (4), pp. 887–891, and can be synthesized in accordance with the synthetic method described therein.

The reference cited above gives no description of the possibility of the use of the compound described therein as a color photographic coupler.

The coupler of the present invention can be used in the range normally from $1\times10^{-3}$ mol to 1 mol, preferably from $1\times10^{-2}$ mol to $8\times10^{-1}$ mol per mol of silver halide.

The coupler of the present invention can be used in combination with other kinds of couplers.

The coupler of the present invention permits application of the methods and techniques used for ordinary dye forming couplers.

The coupler of the present invention can be used as a color photographic material whether it is processed by the coupler-in-developer process or the coupler-in-emulsion process.

When using for the coupler-in-developer process, the coupler of the present invention can be dissolved in an aqueous solution of alkali or an organic solvent such as alcohol and added to the processing solution.

When using as a color photographic light-sensitive material processed by the coupler-in-emulsion process, the coupler of the present invention is contained in the photographic light-sensitive material.

Typically, it is a preferred mode of the use of the coupler of the present invention to add it to a silver halide emulsion and coat the emulsion on the support to form a color light-sensitive material. The coupler of the present invention is applicable to color photographic light-sensitive materials such as color negative films, color positive films and color printing paper.

The light-sensitive material incorporating the coupler of the present invention, including color printing paper, may be of the monochrome type or the multiple color type. In multiple color light-sensitive materials, the coupler of the present invention may be contained in any layer, but it is the common practice to add it to a red-sensitive silver halide emulsion layer. The multiple color light-sensitive material has dye image forming units possessing light sensitivity in the respective spectral regions of the three primary colors. Each unit can comprise a single or multiple emulsion layer possessing light-sensitivity in a given spectral region.

The light-sensitive material structural layers, including the image forming unit layers, can be arranged in various orders. A typical multiple color light-sensitive material comprises a support and a cyan dye image forming unit of at least one red-sensitive silver halide emulsion layer containing at least one cyan coupler, a magenta dye image forming unit of at least one green-sensitive silver halide emulsion layer containing at least one magenta coupler and a yellow dye image forming unit of at least one blue-sensitive silver halide emulsion layer containing at least one yellow coupler, which dye image forming units are provided on the support.

The light-sensitive material can have additional layers such as filter layers, interlayers, protective layers and undercoating layers.

The coupler of the present invention is added to emulsion in accordance with a conventional method. For example, the coupler of the invention is dissolved in a high boiling organic solvent having a boiling point of over 175° C. such as tricresyl phosphate or dibutyl phthalate or a low boiling solvent such as butyl acetate or butyl propionate or a mixture thereof prepared as necessary, after which it is mixed with a surfactant-containing aqueous solution of gelatin and then emulsified using a high rotating mixer or colloid mill, after which it is added to the silver halide emulsion.

The silver halide composition of silver halide emulsion preferably used in light-sensitive materials incorporating the coupler of the present invention is silver chloride, silver chlorobromide or silver chloroiodobromide. A mixture such as of silver chloride and silver bromide is also acceptable.

When a silver halide emulsion layer is used for color printing paper, especially high developability is required; therefore, the halogen composition of the silver halide preferably contains a chlorine atom, with more preference given to silver chloride, or silver chlorobromide or silver chloroiodobromide containing at least 1% silver chloride.

The silver halide emulsion is chemically sensitized by a conventional method. It can also be optically sensitized in the desired wavelength band.

The silver halide emulsion may be formulated with various compounds which are known as antifogging agents or stabilizers in the photographic industry for the purpose of preventing fogging and/or keeping the photographic performance stable during production, storage and processing of the light-sensitive material.

Color light-sensitive materials incorporating the coupler of the present invention may contain antistaining agents, dye image stabilizers, UV absorbents, antistatic agents, matting agents, surfactants and other additives in common use in light-sensitive materials.

With respect to these additives, the description given in Research Disclosure No. 176, 22–31 (December 1978), for instance, serves as reference.

Color photographic light-sensitive materials incorporating the coupler of the present invention are capable of forming images by a known color developing process.

Color photographic light-sensitive materials incorporating the coupler of the present invention may contain a color developing agent as such or as a precursor thereof in a hydrophilic colloid layer, and can be processed using an alkaline activating bath.

Color photographic light-sensitive materials incorporating the coupler of the present invention are bleached and stabilized after color development. Bleaching may be conducted simultaneously with fixation.

Fixation is normally followed by washing. Washing may be replaced by stabilization, and both may be conducted in combination.

EXAMPLES

The present invention is hereinafter described in more detail by means of the following examples.

EXAMPLE 1

Synthesis of Exemplified Compound 31

Exemplified Compound 31 was synthesized in the following scheme.

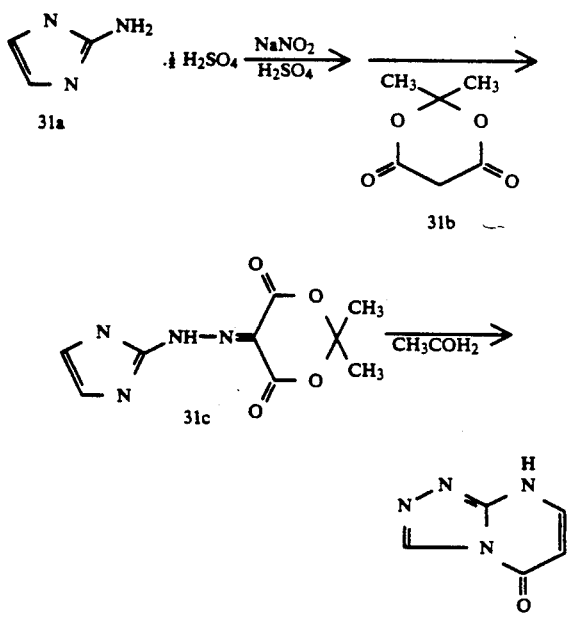

i) Synthesis of Intermediate 31c 3.46 g (26.2 mmol) of 2-aminoimidazole 1/2 sulfate 31a was dissolved in 30 ml of 2 mol/l sulfuric acid and cooled to −5° C. To this solution was added drop by drop 5 ml of an aqueous solution of 1.97 g (28.5 mmol) of sodium nitrite. After reaction at −5° C. for 30 more minutes, pH was adjusted to 6. Then, this solution was added drop by drop at 0° C. to 30 ml of an aqueous solution of 3.77 g (26.2 mmol) of 31b, followed by 1 hour of reaction at 0° C.

After completion of the reaction, the resulting crystal was filtered, washed with cold water and then purified by column chromatography to yield 5.20 g (yield 83%) of Intermediate 31c.

ii) Synthesis of Exemplified Compound 31

2.0 g (8.40 mmol) of 31c was dissolved in 200 ml of acetic acid and refluxed under boiling conditions for 24 hours. After completion of the reaction, the solvent was distilled off under reduced pressure. The resulting residue was washed with water and recrystallized from ethanol to yield 1.05 g (yield 92%) of Exemplified Compound 31. Its melting point was 265° C.

This compound was structurally identified by NMR, IR and MASS.

EXAMPLE 2

The following layers were coated on a paper support laminated with polyethylene on both faces in the order shown below from the support side to yield a red-sensitive color light-sensitive material sample 1. The amount of compounds added is expressed per $m^2$ unless otherwise stated (the amount of silver halide is expressed as silver).

Layer 1: Emulsion layer

A red-sensitive emulsion layer comprising 1.2 g of gelatin, 0.30 g of a red-sensitive silver chlorobromide emulsion (silver chloride content 96 mol%) and $9.1 \times 10^{-4}$ mol of Comparative Coupler a in solution in 1.35 g of dioctyl phosphate.

Layer 2: Protective Layer

A protective layer containing 0.50 g of gelatin. As a hardener, sodium salt of 2,4-dichloro-6-hydroxy-S-triazine was added to 0.017 g per gram of gelatin.

A surfactant and an antifungal agent (a mixture of 2-methylisothiazol-3-one and 5-chloro-2-methylisothiazol-3-one) was added to the sample.

Samples 2 through 8 were prepared in the same manner as with Sample 1 except that Comparative Coupler a was replaced with the couplers listed in Table 1 (the same molar amount as with Comparative Coupler a).

Samples 1 through 8 thus obtained were each subjected to exposure through an optical wedge in accordance with a conventional method and then processed using the following procedures.

| Procedures | | |
| --- | --- | --- |
| Color development | 38° C. | 3 minutes 30 seconds |
| Bleach-fixation | 38° C. | 1 minute 30 seconds |
| Stabilization | 25 to 30° C. | 3 minutes |
| Drying | 75 to 80° C. | 2 minutes |

The processing solutions used in the respective processing procedures had the following compositions:

| Color developer | |
| --- | --- |
| Benzyl alcohol | 15 ml |
| Ethylene glycol | 15 ml |
| Potassium sulfite | 2.0 g |
| Potassium bromide | 0.7 g |
| Sodium chloride | 0.2 g |
| Potassium carbonate | 30.0 g |
| Hydroxylamine sulfate | 3.0 g |
| Polyphosphoric acid (TPPS) | 2.5 g |
| 3-methyl-4-amino-N-ethyl-N-(β-methanesulfonamidoethyl)aniline sulfate | 5.5 g |
| Brightening agent(4,4'-diaminostylbenedisulfonic acid derivative) | 1.0 g |
| Potassium hydroxide | 2.0 g |

Water was added to make a total quantity of 1 l, and pH was adjusted to 10.20.

| Bleach-fixer | |
| --- | --- |
| Ferric ammonium ethylenediaminetetraacetate dihydrate | 60 g |
| Ethylenediaminetetraacetic acid | 3 g |
| Ammonium thiosulfate (70% solution) | 100 ml |
| Ammonium sulfite (40% solution) | 27.5 ml |

Potassium carbonate or glacial acetic acid was added to obtain a pH of 7.1, and water was added to make a total quantity of 1 l.

| Stabilizer | |
| --- | --- |
| 5-chloro-2-methyl-4-isothiazolin-3-one | 1.0 g |
| Ethylene glycol | 10 g |

Water was added to make a total quantity of 1 l.

Samples 1 through 8 thus processed were subjected to densitometry using a densitometer (KD-7 model, produced by Konica Corporation). The processed samples were each kept standing in a high-temperature high-humidity (60° C., 80% RH) atmosphere for 14 days, after which dye image heat/moisture fastness was determined.

Each sample was irradiated with light using a xenon fade-O-meter for 10 days and then subjected to densitometry to determine the light fastness.

The results are shown in Table 1. Values for dye image heat/moisture fastness and light fastness are expressed in percent dye residual rate obtained the heat/moisture and light fastness tests, relative to an initial density of 1.0.

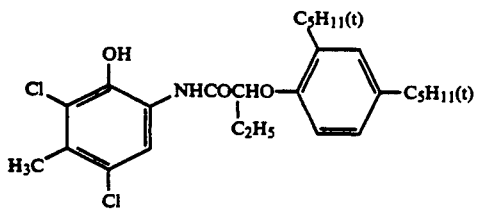

TABLE 1

| Sample No | Coupler used | Dye residual rate (%) Heat/moisture fastness | Light fastness |
|---|---|---|---|
| 1 | Comparative a | 60 | 81 |
| 2 | Exemplified 3 | 86 | 85 |
| 3 | Exemplified 6 | 87 | 83 |
| 4 | Exemplified 10 | 89 | 82 |
| 5 | Exemplified 18 | 90 | 84 |
| 6 | Exemplified 25 | 87 | 88 |
| 7 | Exemplified 36 | 88 | 83 |
| 8 | Exemplified 41 | 91 | 84 |

From the results shown in Table 1, it is evident that the samples incorporating the coupler of the present invention offer higher dye residual rate and have better heat/moisture fastness and light fastness in comparison with the sample incorporating the comparative coupler.

EXAMPLE 3

The following layers were coated on a subbed triacetate film in the order shown below from the support side to yield a red-sensitive color light-sensitive material sample 9. The amount of compounds added is expressed per $m^2$ unless otherwise stated (the amount of silver halide is expressed as silver).

Layer 1: Emulsion Layer

A red-sensitive emulsion layer comprising 1.4 g of gelatin, 1.5 g of a red-sensitive silver iodobromide emulsion (silver iodide content 4 mol %) and $8.0 \times 10^{-4}$ mol of Comparative Coupler b in solution in 1.1 g of tricresyl phosphate.

Layer 2: Protective Layer

A protective layer containing 1.5 g of gelatin. As a hardener, sodium salt of 2,4-dichloro-6-hydroxy-S-triazine was added to 0.017 g per gram of gelatin.

A surfactant and an antifungal agent (a mixture of 2-methylisothiazol-3-one and 5-chloro-2-methylisothiazol-3-one) was added to the sample.

Samples 10 through 16 according to the present invention were prepared in the same manner as with sample 9 except that Comparative Coupler b was replaced with the couplers listed in Table 2 (the same molar amount as with Comparative Coupler b).

The film samples thus obtained were each subjected to exposure through an optical wedge in accordance with a conventional method and then processed using the following color processing procedures.

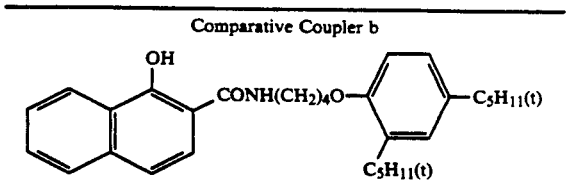

| Processing procedures (38° C.) | Processing time |
|---|---|
| Color development | 3 minutes 15 seconds |
| Bleaching | 6 minutes 30 seconds |
| Washing | 3 minutes 15 seconds |
| Fixation | 6 minutes 30 seconds |
| Washing | 3 minutes 15 seconds |
| Stabilization | 1 minute 30 seconds |
| Drying | |

The processing solutions used in the respective processing procedures had the following compositions:

| Color developer | |
|---|---|
| 4-amino-3-methyl-N-ethyl-N-($\beta$-hydroxyethyl) aniline sulfate | 4.75 g |
| Anhydrous sodium sulfite | 4.25 g |
| Hydroxylamine ½ sulfate | 2.0 g |
| Anhydrous potassium carbonate | 37.5 g |
| Sodium bromide | 1.3 g |
| Trisodium nitrilotriacetate monohydrate | 2.5 g |
| Potassium hydroxide | 1.0 g |

Water was added to make a total quantity of 1 l, and sodium hydroxide was added to obtain a pH of 10.6.

| Bleacher | |
|---|---|
| Iron ammonium ethylenediaminetetraacetate | 100.0 g |
| Diammonium ethylenediaminetetraacetate | 10.0 g |
| Ammonium bromide | 150.0 g |
| Glacial acetic acid | 10.0 g |

Water was added to make a total quantity of 1 l, and aqueous ammonia was added to obtain a pH of 6.0.

| Fixer | |
|---|---|
| Ammonium thiosulfate | 175.0 g |
| Anhydrous sodium sulfite | 8.6 g |
| Sodium metasulfite | 2.3 g |

Water was added to make a total quantity of 1 l, and acetic acid was added to obtain a pH of 6.0.

| Stabilizer | |
|---|---|
| Formalin (37% by weight) | 1.5 ml |
| Konidax (produced by Konica Corporation) | 7.5 ml |

Water was added to make a total quantity of 1 l.

Samples 9 through 16 thus processed were subjected to transmission densitometry using a densitometer (KD-7R model, produced by Konica Corporation). The processed samples were each kept standing in a high-temperature high-humidity (60° C., 80% RH) atmosphere for 14 days, and dye image heat/moisture fastness was determined.

Each sample was irradiated with light using a xenon fade-O-meter for 10 days and light fastness was determined.

The results are shown in Table 2. Values for dye image heat/moisture fastness and light fastness are expressed in percent dye residual rate obtained after the heat/moisture and light fastness tests, relative to an initial density of 1.0.

TABLE 2

| Sample No | Coupler used | Dye residual rate (%) | |
|---|---|---|---|
| | | Heat/moisture fastness | Light fastness |
| 9 | Comparative b | 70 | 80 |
| 10 | Exemplified 4 | 85 | 80 |
| 11 | Exemplified 7 | 89 | 81 |
| 12 | Exemplified 19 | 87 | 82 |
| 13 | Exemplified 23 | 91 | 85 |
| 14 | Exemplified 32 | 90 | 85 |
| 15 | Exemplified 34 | 92 | 83 |
| 16 | Exemplified 43 | 87 | 84 |

From the results shown in Table 2, it is evident that the samples incorporating the coupler of the present invention offer higher dye residual rate and have better heat/moisture fastness in comparison with the sample incorporating the comparative coupler. The light fastness is also equivalent to, or higher than, that obtained with the comparative coupler.

EXAMPLE 4

The following layers were coated on a triacetyl cellulose film support in the order shown below from the support side to yield a red-sensitive color reversal photographic light-sensitive material samples 17 through 22 which contain the couplers listed in Table 3.

Layer 1: Emulsion Layer

A red-sensitive emulsion layer comprising 1.4 g of gelatin, 0.5 g of a red-sensitive silver chlorobromide emulsion (silver chloride content 96 mol %) and $9.1 \times 10^{-4}$ mol of a coupler shown in Table 3 in solution in 1.5 g of dibutyl phthalate.

Layer 2: Protective Layer

A protective layer containing 0.5 g of gelatin. As a hardener, sodium salt of 2,4-dichloro-6-hydroxy-S-triazine was added to 0.017 g per gram of gelatin.

A surfactant and an antifungal agent (a mixture of 2-methylisothiazol-3-one and 5-chloro-2-methylisothiazol-3-one) was added to the sample.

The samples thus obtained were each subjected to exposure through an optical wedge in accordance with a conventional method and then processed using the following procedures.

| Reversal process Procedure | Time | Temperature |
|---|---|---|
| First development | 6 minutes | 38° C. |
| Washing | 2 minutes | 38° C. |
| Reversal | 2 minutes | 38° C. |
| Color development | 6 minutes | 38° C. |
| Adjustment | 2 minutes | 38° C. |
| Bleaching | 6 minutes | 38° C. |
| Fixation | 4 minutes | 38° C. |
| Washing | 4 minutes | 38° C. |
| Stabilization | 1 minute | 38° C. |
| Drying | | Normal temperature |

The processing solutions used in the respective processing procedures had the following compositions:

| First developer | |
|---|---|
| Sodium tetrapolyphosphate | 2 g |
| Sodium sulfite | 20 g |
| Hydroquinone monosulfonate | 30 g |
| Sodium carbonate monohydrate | 30 g |
| Sodium sulfite | 12 g |
| Sodium ethylenediaminetetraacetate dihydrate | 8 g |
| Thioglycerol | 0.4 ml |
| Glacial acetic acid | 3 ml |

Water was added to make a total quantity of 1000 ml.

| Bleacher | |
|---|---|
| Sodium ethylenediaminetetraacetate dihydrate | 2.0 g |
| Iron (III) ammonium ethylenediaminetetraacetate dihydrate | 120.0 g |
| Potassium bromide | 100.0 g |

Water was added to make a total quantity of 1000 ml.

| Fixer | |
|---|---|
| Ammonium thiosulfate | 80.0 g |
| Sodium sulfite | 5.0 g |
| Sodium bisulfite | 5.0 g |

Water was added to make a total quantity of 1000 ml.

| Stabilizer | |
|---|---|
| Formalin (37% by weight) | 5.0 ml |
| Konidax (produced by Konica Corporation) | 5.0 ml |

Water was added to make a total quantity of 1000 ml.

The samples thus processed were each examined for dye image heat/moisture fastness and light fastness in the same manner as in Example 3. The results are shown in Table 3.

TABLE 3

| Sample No | Coupler used | Dye residual rate (%) | |
|---|---|---|---|
| | | Heat/moisture fastness | Light fastness |
| 17 | Comparative a | 59 | 81 |
| 18 | Exemplified 8 | 90 | 84 |
| 19 | Exemplified 12 | 85 | 80 |
| 20 | Exemplified 16 | 88 | 81 |
| 21 | Exemplified 35 | 91 | 83 |
| 22 | Exemplified 44 | 91 | 82 |

From the results shown in Table 3, it is evident that the samples incorporating the coupler of the present invention offer higher dye residual rate and have better heat/moisture fastness in comparison with the sample incorporating the comparative coupler. The light fastness is also equivalent to, or higher than, that obtained with the comparative coupler.

The dye images formed with the coupler of the present invention are fast to heat/moisture and light.

What is claimed is:

1. A color photographic material having a substrate and a light sensitive silver halide emulsion layer containing a coupler represented by a formula

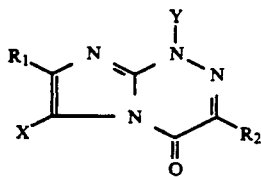

wherein $R_1$, $R_2$ and Y independently represent a hydrogen atom or substituent, X represents a hydrogen atom or an atom or group capable of splitting off upon reaction with the oxidation product of a color developing agent.

2. A color photographic material according to claim 1, wherein Y is a hydrogen atom.

3. A color photographic material according to claim 1, wherein $R_1$ and $R_2$ independently represent a hydrogen atom or alkyl, aryl, anilino, acylamino, sulfonamide, alkylthio, arylthio, alkenyl, cycloalkyl groups, halogen atom, cycloalkenyl, alkinyl, heterocyclic, sulfonyl, sulfinyl, phosphonyl, acyl, carbamoyl, sulfamoyl, cyano, alkoxy, sulfonyloxy, aryloxy, heterocyclic oxy, siloxy, acyloxy, carbamoyloxy, amino, alkylamino, imide, ureide, sulfamoylamino, alkoxycarbonylamino, aryloxycarbonylamino, akloxycarbonyl, aryloxycarbonyl, heterocyclic thio, thioureide, carboxyl, hydroxy, mercapto, nitro and sulfonic acid groups, and spiro compound groups and bridged hydrocarbon compound groups.

4. A color photographic material according to claim 1, wherein $R_1$ and $R_2$ independently represent a hydrogen atom or alkyl, aryl, anilino, acylamino, sulfonamide, alkylthio, arylthio, alkenyl and cycloalkyl groups.

5. A color photographic material according to claim 4, wherein $R_1$ and $R_2$ independently represent an alkyl, aryl, anilino, acylamino or sulfonamide.

6. A color photographic material according to claim 1, wherein X is a halogen atom.

7. A color photographic material according to claim 1, wherein X is a chlorine or bromine atom.

8. A color photographic material having a substrate and a light sensitive silver halide emulsion layer containing a cyan color forming coupler represented by a formula

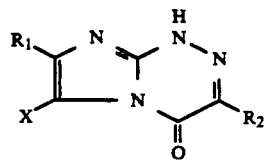

wherein $R_1$ and $R_2$ independently represent an alkyl, aryl, anilino, acylamino or sulfonamide, X represents a hydrogen, chlorine or bromine atom.

* * * * *